(12) United States Patent
Liu

(10) Patent No.: US 9,072,322 B2
(45) Date of Patent: Jul. 7, 2015

(54) MOUTHPIECE DEVICE OF ELECTRONIC CIGARETTE

(75) Inventor: Qiuming Liu, Guangdong (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 130 days.

(21) Appl. No.: 13/392,096

(22) PCT Filed: Dec. 23, 2011

(86) PCT No.: PCT/CN2011/084586
§ 371 (c)(1),
(2), (4) Date: Feb. 24, 2012

(87) PCT Pub. No.: WO2013/091251
PCT Pub. Date: Jun. 27, 2013

(65) Prior Publication Data
US 2013/0160765 A1    Jun. 27, 2013

(51) Int. Cl.
*A24F 47/00* (2006.01)
*A61M 15/06* (2006.01)

(52) U.S. Cl.
CPC ............ *A24F 47/008* (2013.01); *A24F 47/002* (2013.01); *A61M 15/06* (2013.01)

(58) Field of Classification Search
CPC .... A61M 15/06; A24F 47/002; A24F 47/004; A24F 47/008
USPC ............. 128/202.21, 203.17, 203.23, 203.27; 131/194, 270, 273
See application file for complete search history.

(56) References Cited

U.S. PATENT DOCUMENTS 5,708,258 A * 1/1998 Counts et al. ................. 219/535
8,079,371 B2 * 12/2011 Robinson et al. ............. 131/200
(Continued)

FOREIGN PATENT DOCUMENTS

GB         2190000 A  * 11/1987  ............ A61M 16/16

OTHER PUBLICATIONS

"Granular Molding Powders". DuPont. Accessed via Wayback Machine Internet Archive on Nov. 25, 2013. https://web.archive.org/web/20071125094733/http://www2.dupont.com/Teflon__Industrial/en_US/products/product_by_name/tefl on_ptfe/granular.html.*

(Continued)

*Primary Examiner* — Justine Yu
*Assistant Examiner* — Kathrynn Reilly
(74) *Attorney, Agent, or Firm* — Cheng-Ju Chiang

(57) ABSTRACT

The present invention relates to a mouthpiece device of an electronic cigarette, includes an atomizing device for vaporizing tobacco substance into aerosol, a reservoir for storing tobacco substance and a guiding tube for guiding tobacco substance from the reservoir to the atomizing device, which are all set in a shell. The guiding tube has one end inserted in the reservoir and the other end communicated with atomizing device. The mouthpiece device further includes a preheating device for heating solid tobacco substance in the reservoir to generate liquid. The preheating device is set in the end of the reservoir near the guiding tube, and seals solid tobacco substance in the reservoir. The present invention solves existing problems such as fluid leakage, complicate manufacturing, high cost, bad heat insulation and filtering aerosol; and obtains perfect leakage proof, simple manufacturing, lower cost, good heat insulation and well filtering aerosol.

14 Claims, 6 Drawing Sheets

(56) References Cited

U.S. PATENT DOCUMENTS

2007/0102013 A1* 5/2007 Adams et al. ............... 131/273
2011/0011396 A1* 1/2011 Fang ...................... 128/202.21
2011/0126848 A1* 6/2011 Zuber et al. ................ 131/329
2011/0155153 A1* 6/2011 Thorens et al. ............. 131/329
2011/0253135 A1* 10/2011 Hale et al. ............... 128/202.21
2011/0290244 A1* 12/2011 Schennum ............... 128/200.23
2012/0037175 A1* 2/2012 Cantrell et al. ............. 131/353

OTHER PUBLICATIONS

Rimpex Rubber. "Horizontal Vertical Compression Type Liquid Silicone Rubber Injection Molding Machine DCZ Series". Saved Mar. 17, 2009. Accessed Apr. 1, 2014. https://web.archive.org/web/20090317084958/http://www.rubberimpex.com/RubberMachinery/GDRMO2Catalogue.htm.*

* cited by examiner

MOUTHPIECE DEVICE OF ELECTRONIC CIGARETTE

BACKGROUND OF THE INVENTION

The present invention relates to an electronic cigarette, especially to a mouthpiece device of the electronic cigarette.

Referring to FIG. 1, a mouthpiece device of the existing electronic cigarette comprises an inhaling shell 1', atomizing device 2', guiding tube 3' for guiding tobacco substance flowing therethrough, stopper 4', and cap 5'.

The shell 1' comprises a reservoir 11' for storing tobacco substance therein and an aerosol passage 12' for allowing aerosol to pass therethrough. The atomizing device 2' comprises an atomizer 21' and an atomizing cup assembly 22' for holding the atomizer 21'. The atomizing cup assembly 22' is composed of a support seat 221', a ceramic seat 222' and a foam-nickel unit 223'. The guiding tube 3' has one end thereof connected with the reservoir 11' through a metal frame 6' so as to guide the tobacco substance from the reservoir 11' to the atomizing cup assembly 22'. The stopper 4' is inserted in the reservoir 11' at one end facing the atomizing device 2', and the cap 5' is used for sealing the other end of the reservoir 11'.

However, the existing mouthpiece device of the electronic cigarette has such disadvantages that: since tobacco substance in the reservoir is liquid at a normal atmospheric temperature, during storage or use, the positions where tobacco substance flows out or where the guiding tube 3' is engaged with the stopper 4', easily spill tobacco substance out, which presents a hidden trouble of fluid-leakage; it is very complicated to manufacture and assemble the atomizing cup assembly 22', the manufacturing cost is high; the ceramic seat 222' and foam-nickel unit 223' directly contact with inner wall of the shell 1', which results unsatisfactory heat insulation, and the temperature at outer wall of the shell 1' is relatively high even to be felt burning hand, then the electronic cigarette cannot be used; the metal frame 6' does not facilitate guiding tobacco substance, but raises the manufacturing cost; moreover, the cap 5' is set at an inhaling end of the shell 1', the aerosol passage 12' directly extends to outside of the shell 1', therefore, tobacco particles will flow together with the aerosol from the aerosol passage 12' to outside of the shell 1', and thus fail to be filtered.

BRIEF SUMMARY OF THE INVENTION

A main object of the present invention is to provide a mouthpiece device of an electronic cigarette, which has good leakage-proof performance.

Another object of the present invention is to provide a mouthpiece device of an electronic cigarette, which facilitates manufacturing, reduces cost, and has good heat insulation.

A further object of the present invention is to provide a mouthpiece device of an electronic cigarette, which perfectly filters tobacco substance.

To obtain the above object, a mouthpiece device of an electronic cigarette comprises an atomizing device for vaporizing tobacco substance into aerosol, a reservoir for storing tobacco substance and a guiding tube for guiding tobacco substance from the reservoir to the atomizing device, which are all set in an inhaling shell. The guiding tube has one end inserted in the reservoir and the other end communicated with the atomizing device. The mouthpiece device further comprises a preheating device for heat solid tobacco substance stored in the reservoir to generate liquid tobacco substance. The preheating device is set in the reservoir at the end near the guiding tube, and seals the solid tobacco substance in the reservoir.

Further, the preheating device comprises a heat-insulation layer, a heating layer, and a heat-conductive layer. The heating layer is disposed between the heat-insulation layer and the heat-conductive layer. The heat-insulation layer is disposed in the reservoir at the end where the guiding tube is inserted, and tightly fitted in the reservoir. The heat-conductive layer seals solid tobacco substance in the reservoir.

Further, the heating layer is electric heat wire, electric heat film, or electric heat coating.

Further, the guiding tube inserts in the reservoir and respectively penetrates through the heat-insulation layer, the heating layer and the heat-conductive layer. The engagement between the heat-conductive layer and the guiding tube is an interference fit, and seal material is inserted between the heat-conductive and the guiding tube.

Further, the mouthpiece device comprises a stopper which is disposed at an end of the reservoir. One end of the guiding tube is inserted through the stopper and extends to the reservoir. The stopper defines a tube hole, and the guiding tube is engaged in the tube hole by an interference fit with sealing material circulary inserted therebetween.

Further, the atomizing device comprises an atomizing cup with an atomizing chamber therein, and an atomizer held in the atomizing chamber. The atomizing cup is made by an integrated molding process in a mould.

Further, the atomizing cup is shaped as a cylinder, has a figuration and dimension adapted to an inner wall of the inhaling shell. The atomizing cup comprises a mounting seat disposed in the atomizing chamber for holding the atomizer, and wire-through holes for passing electric wire therethrough. The wire-through holes are defined in the atomizing cup and communicated with the atomizing chamber. The atomizing cup also defines a through heat-dissipation hole in center thereof.

Further, the atomizing device comprises a filter device set in the inhaling shell for depositing tobacco particles in aerosol, and an aerosol passage for transmitting aerosol to outside of the inhaling shell.

Further, the filter device comprises a cap for sealing an end of the reservoir. The cap defines an air slot for depositing tobacco particles on surface thereof, and suction hole for air communicating in and out of the inhaling shell. The air slot is communicated with the aerosol passage, and the suction hole is also communicated with the aerosol passage.

Further, a filter layer is set on an inner wall of the aerosol passage according to a cross section of the aerosol passage.

The advantages of the present invention are that: the preheating device of the electric cigarette is used for heating solid tobacco substance to generate liquid tobacco substance which is solidified and stored in the reservoir at first, and seals solid or liquid tobacco substance in the reservoir; in smoking, solid tobacco substance is heated to generate liquid by the preheating device, and is delivered to the atomizing device by the guiding tube; since tobacco substance is solidified and stored in the reservoir at first, thus at a normal atmospheric temperature, difficultly leaks out; in use, melt tobacco substance is sealed and separated in the reservoir, the stopper at one end of the reservoir further seals the preheating device in the reservoir, thus tobacco substance is doubly sealed and separated, difficultly leaks out; moreover, the mouthpiece device has an integrated atomizing cup, which facilitates manufacturing and reduces cost; and the atomizing cup has good heat insulation performance; furthermore, the mouthpiece device has a filtering layer and the cap with filtering function, which renders the mouthpiece device preferably filtering tobacco substance.

A further detailed description to the present invention follows with reference to the drawings.

DETAILED DESCRIPTION OF THE INVENTION

Figure 1:
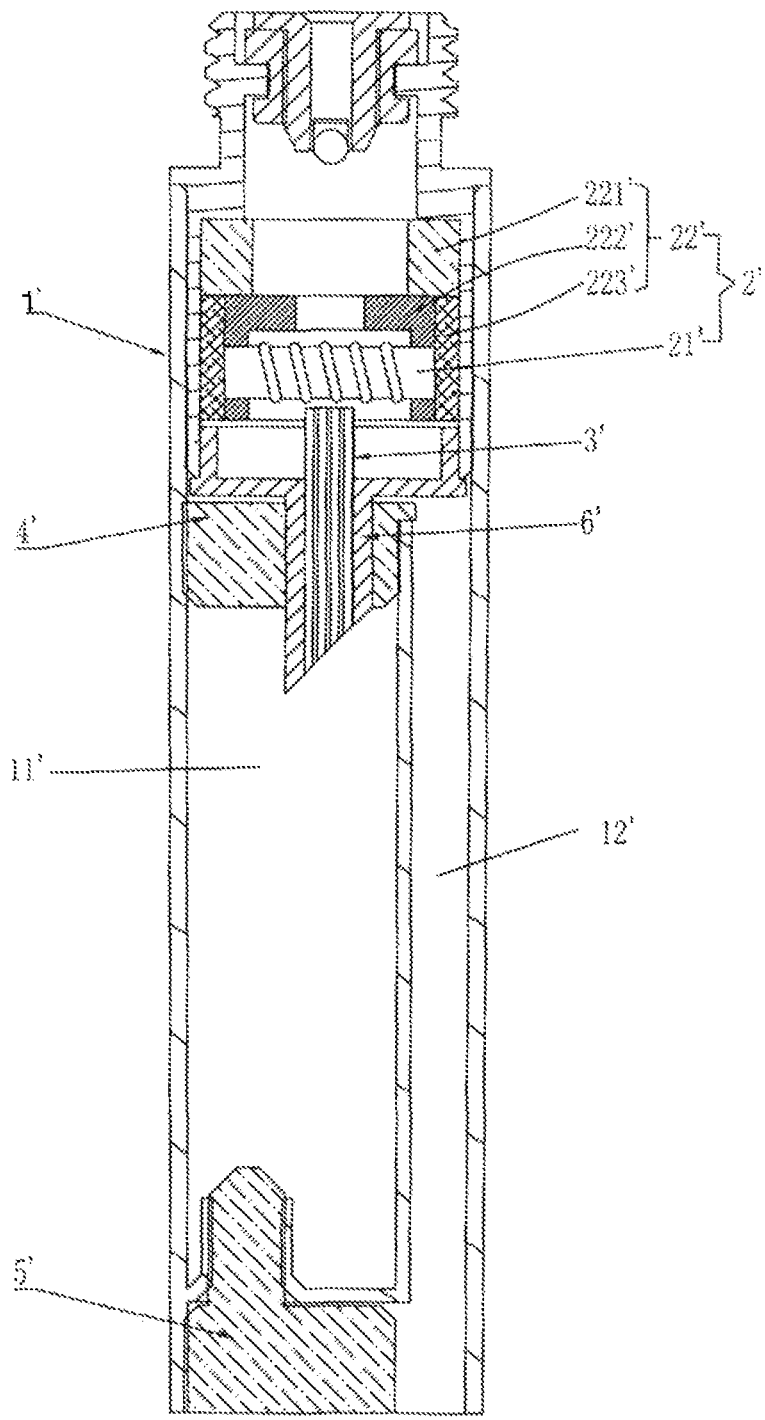
FIG. 1 is a schematic view of a mouthpiece device of an electronic cigarette of prior art.
Figure 2:
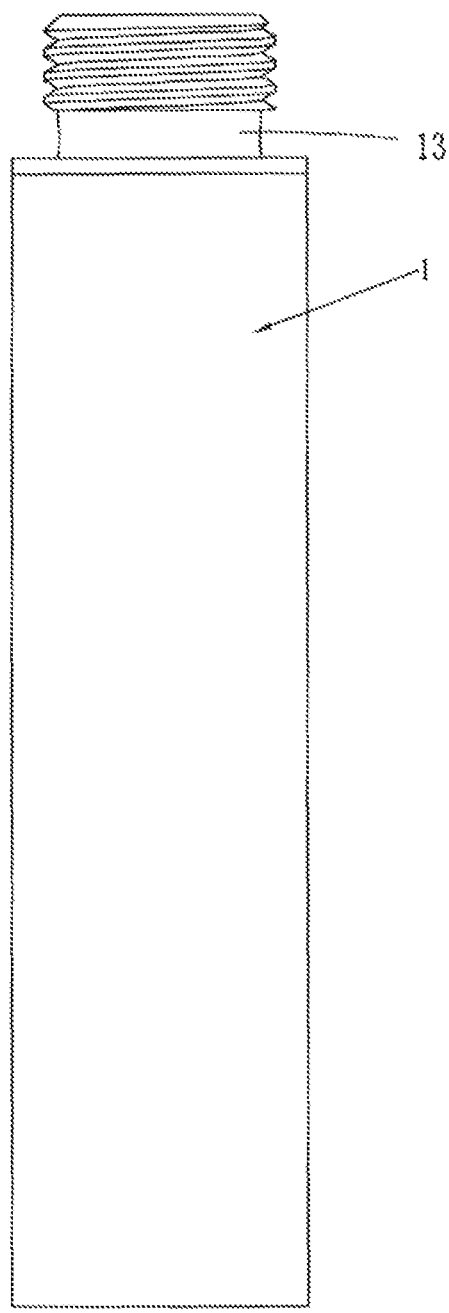
FIG. 2 is a front view of a mouthpiece device of an electronic cigarette of the present invention.
Figure 3:
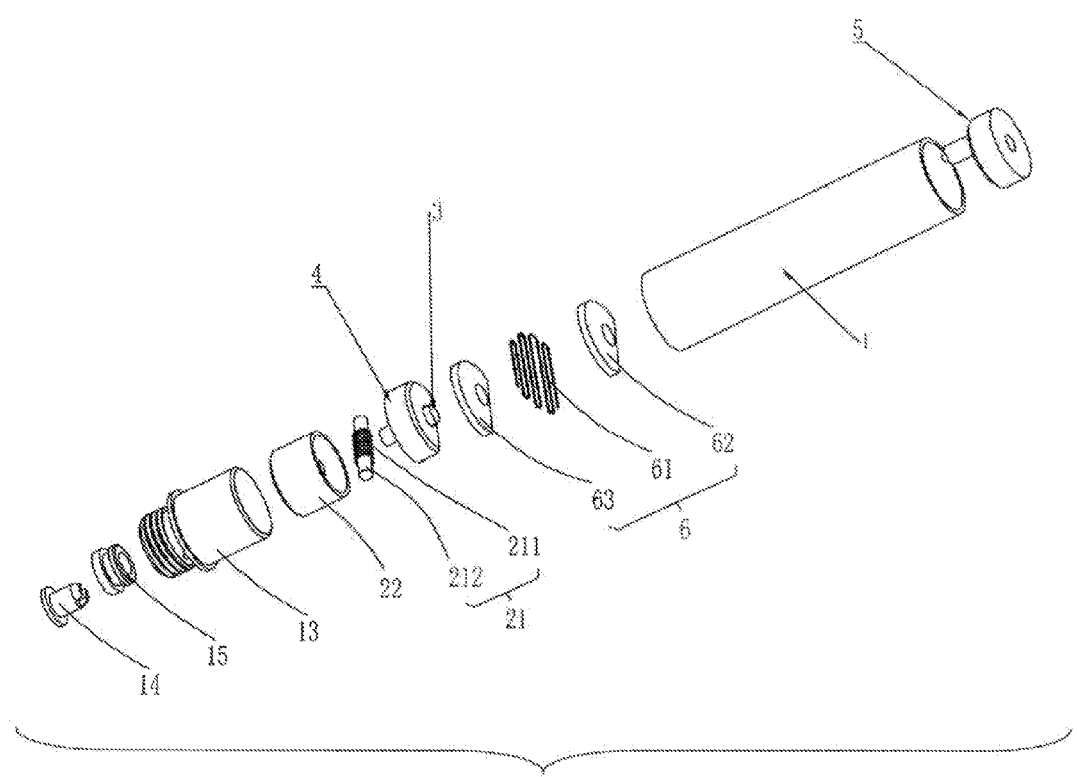
FIG. 3 is an exploded view of the mouthpiece device of the present invention.
Figure 4:
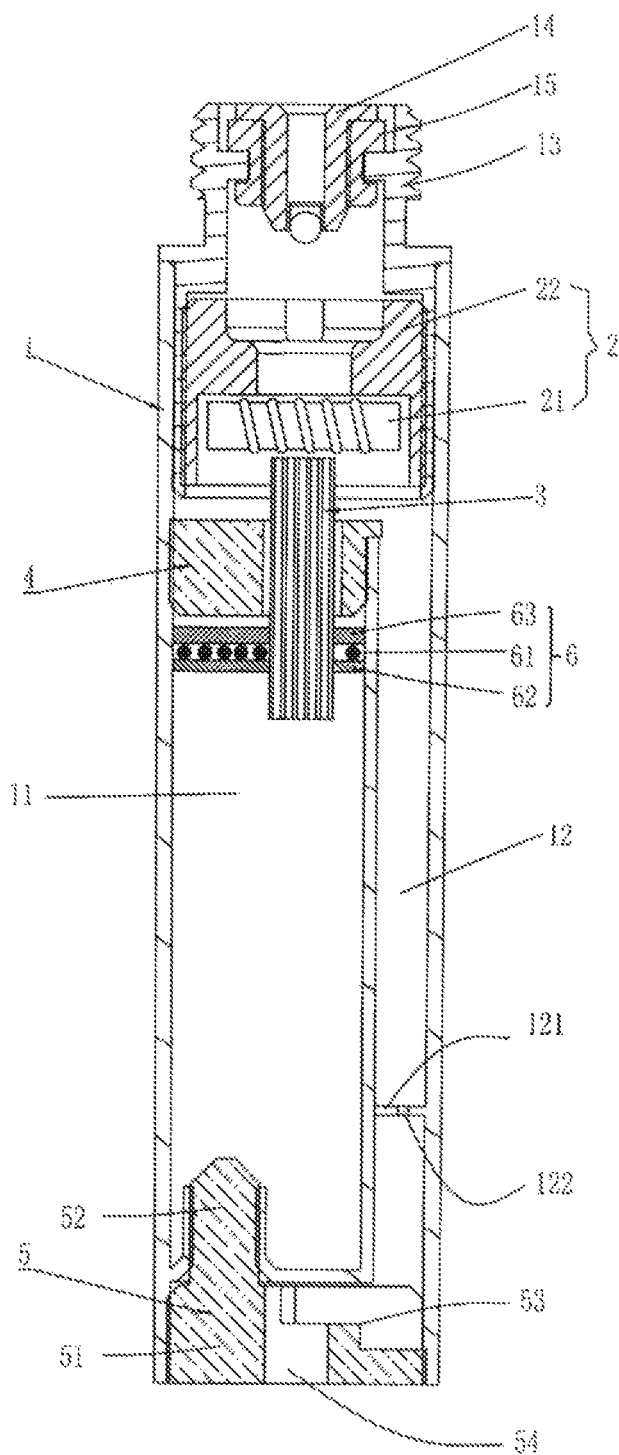
FIG. 4 is a cross-section view of the mouthpiece device of the present invention.
Figure 5:
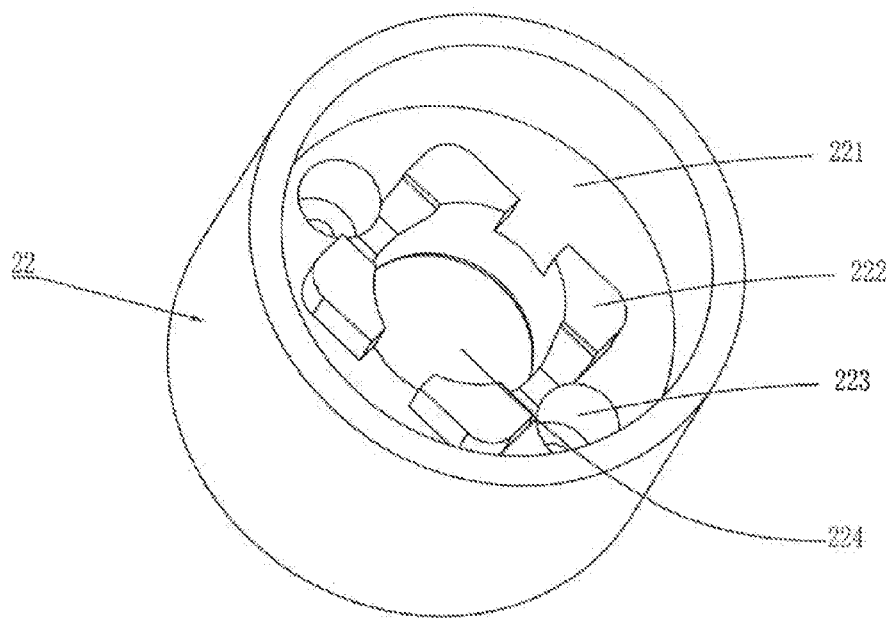
FIG. 5 is a perspective view of an atomizing cup of the mouthpiece device of the present invention.
Figure 6:
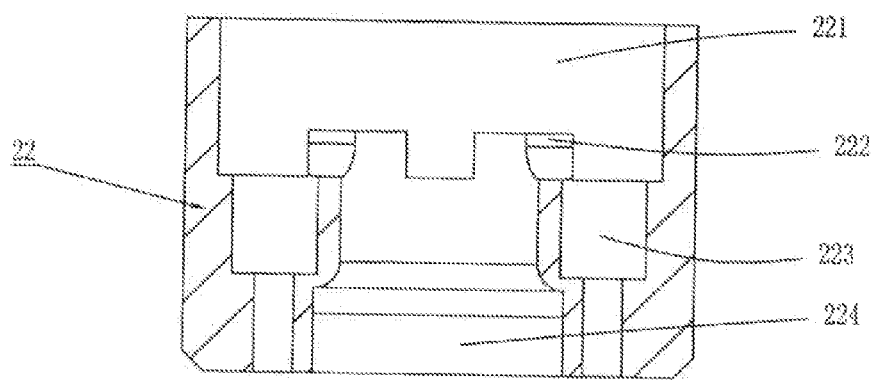
FIG. 6 is a cross-section view of the atomizing cup of the mouthpiece device of the present invention.

Referring to FIGS. 2-8, the present invention provides a mouthpiece device of an electronic cigarette and filtering device thereof. The mouthpiece device comprises an inhaling shell 1, atomizing device 2, guiding tube 3, stopper 4, the filtering device with a cap 5 or cap 5", and preheat device 6 for heating solid tobacco substance to generate liquid tobacco substance.

The inhaling shell 1 comprises a reservoir 11, defining a first opening at one end of the inhaling shell 1 and a second opening opposite to the first opening and facing the atomizing device 2, an aerosol passage 12 alongside the reservoir 11 and defining a third opening at the one end of the inhaling shell 1 to be coplanar with the first opening and a fourth opening opposite to the third opening and facing the atomizing device 2 to be colander with the second opening, a connection element 13, an electrode element 14, and an insulating ring 15. The reservoir 11 is set in the shell 1. In this embodiment, the reservoir 11 is integrated in the shell 1. The reservoir 11 is used to store solid or liquid tobacco substance, has one end thereof set the stopper 4 and the other end set the cap 5. Thus the stopper 4 and cap 5 together seal tobacco substance in the reservoir 11. The aerosol passage 12 is used for aerosol to flow therethrough to an inhaling end of the shell 1 after tobacco substance is vaporized to aerosol by the atomizer 3. A filter layer is set on an inner wall of the aerosol passage 12. The filter is adapted to a cross section of the inner wall. In this embodiment, the filter layer is a filter plate 121 integrated with the aerosol passage 12. The filter plate 121 is set perpendicular to a central line of the aerosol passage 12, and defines at least one filter hole 122 therethrough. The connection element 13 is disposed at a connection end of the shell 1. One end of the connection element 13 with external thread thereon is threadedly connected with a power supply part (not shown) of the electronic cigarette, and the other end thereof is inserted in the shell 1. The connection element 13 defines a cylindrical chamber inside for receiving the atomizing device 3, and defines a mounting groove inside for holding the electrode element 14 therein. The connecting part 13 itself as an electrode of the atomizing device 2 is electrically connected with electrode of the power supply part. The electrode element 14 is fitted in the mounting groove of the connection element 13 in virtue of inserting the insulating ring 15 therebetween. The electrode element 14 has an end contacted with a corresponding electrode of the power supply part so as to energize an electric circuit.

The atomizing device 2 comprises an atomizer 21 and an atomizing cup 22. The atomizer 21 comprises an electric heat wire 211 and an electric heat rod 212. The electric heat wire 211 winds around the heat rod 212, and is mounted in the atomizing cup 22 by means of the heat rod 212. The atomizing cup 22 is made by an integrated molding process in a mould, and comprises an atomizing chamber 221, a mounting seat 222 with fixing groove therein, wire-through holes 223, and a through heat-dissipation hole 224 in center of the atomizing cup 22. The mounting seat 222 with fixing groove therein extends from a bottom of the atomizing chamber 221 up to a certain height, which is used for holding the atomizer 21. The electric heat rod 212 is fixed in the fixing groove of the mounting seat 222. The wire-through holes 223 are used to pass electric wires therethrough, and are disposed in the atomizing cup 22 and communicated to the atomizing chamber 221. There are two wire-through holes in this embodiment. An electric wire connects one end of the heat rod 212, passes one wire-through hole 223 to electrically connect the connection element 13; another electric wire connects the other end of the heat rod 212, passes the other wire-through hole 223 to electrically connect the electrode element 14. The heat-dissipation hole 224 is used to transfer heat from the atomizer to the power supply part. In this embodiment, the atomizing cup 22 is disposed in the shell 1 in virtue of the connection element 13, the atomizing cup 22 is held in the connection element 13, and the dimension and figuration thereof are designed corresponding to the cylindrical chamber of the connection element 13. The material for the atomizing cup 22 has good heat resistance, such as silica gel, which renders the atomizing cup 22 with good heat insulation. The atomizing cup 22 is shaped as a cylinder, and has a diameter larger than that of the cylindrical chamber of connection element 13 so as to be tightly fitted in the connection element 13. The atomizing cup 22 of this embodiment not only facilitates manufacturing of the mouthpiece device, but also reduces the cost. Furthermore, since the atomizing cup 22 is made from silica gel with good heat resistance, which provides a good heat insulation, the temperature at outer wall of the mouthpiece device keeps relative low, and will not burn hand or mouth.

The guiding tube 3 is used to guide tobacco substance from reservoir 11 to atomizing chamber 221 for atomization. The guiding tube 3 has one end thereof directly passing through the stopper 4 and extending in the reservoir 11. The guiding tube 3 is engaged with stopper 4 by interference fit, and is made from glass fiber.

The stopper 4 is used for sealing the reservoir 11, and defines a tube hole therein. The guiding tube 3 is engaged in the hole by interference fit with sealing material inserted therebetween.

Figure 7:
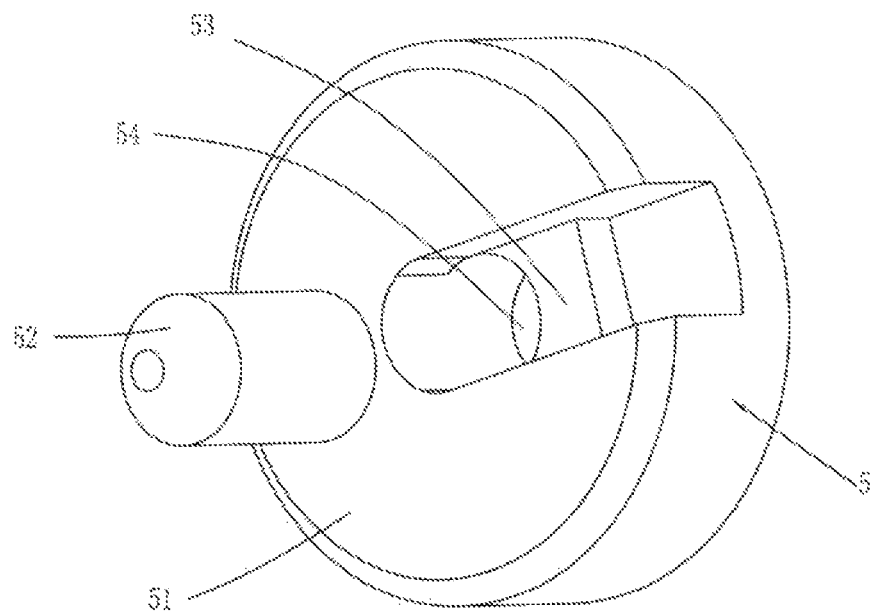
FIG. 7 is a perspective view of a cap of the mouthpiece device in accordance with a first embodiment of the present invention.

Referring to FIG. 7, in the first embodiment, the cap 5 comprises a maid body 51, a plug 52 extending from bottom of the main body, an air slot 53, and a suction hole 54 formed at a center of the cap 5. The cap 5 seals the reservoir 11 in such way that the plug 52 is inserted in the reservoir 11 from the inhaling end of the shell 1. The air slot 53 is stepwise and shaped as letter Z. The air slot 53 is positioned along the same diameter as the plug 52, and is communicated with the aerosol passage 12. The suction hole 54 is used for air communicating between inside and outside of the shell 1. The suction hole 54 is communicated with the air slot 53, and the aerosol passage 12 communicates with the suction hole 54 through the air slot 53. The dimension and figuration of the cap 5 are designed according to inner diameter of the inhaling end of the shell 1. In this embodiment, the cap 5 is shaped as a cylinder, and is made from silica gel. The diameter of the cap 5 is larger than an inner diameter of the shell 1 so that the cap 5 is tightly fitted in the shell 1.

Figure 8:
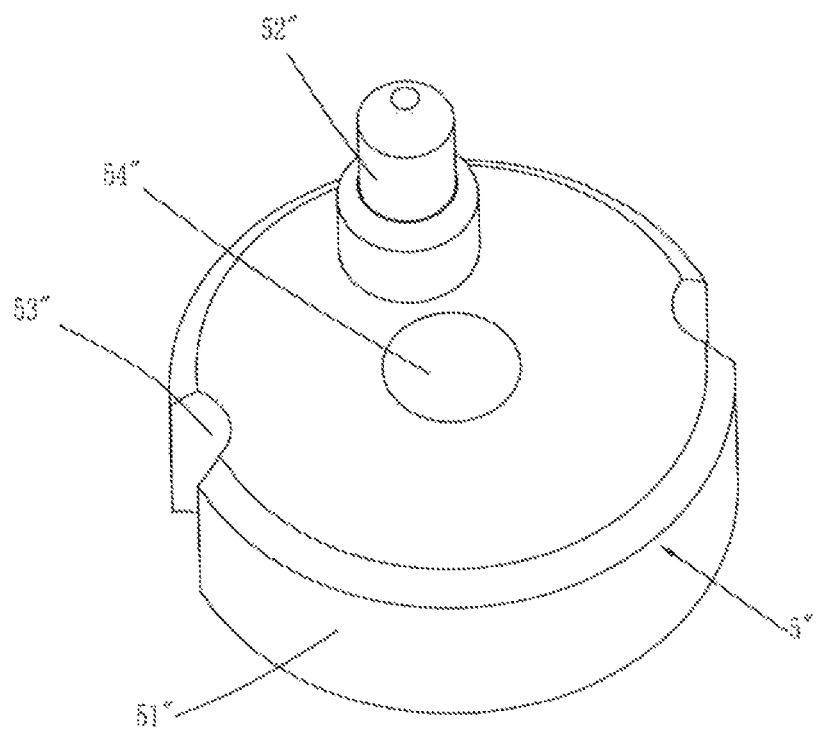
FIG. 8 is a perspective view of the cap of the mouthpiece device in accordance with a second embodiment of the present invention.

Referring to FIG. 8, in the second embodiment, the cap 5" comprises a main body 51", a plug 52" extending from bottom of the main body, air slots 53", and suction hole 54". The cap 5" is mainly similar to cap 5 in the first embodiment, but it is different that the air slot 53" runs through the cap 5" from a top end to a bottom end thereof, is positioned in sidewall of the cap 5", and is depressed towards a center line of the cap. The depressed air slots directly communicate with the aerosol passage 12, and has a cross-section shaped as arc, letter U or V.

The preheating device is used to heat the solid tobacco substance stored in the reservoir 11 to generate liquid tobacco substance, and comprises a heating layer 61, heat-conductive layer 62 and a heat-insulation layer 63.

The heat-insulation layer 63 is positioned in the reservoir at an end where the guiding tube 3 is inserted, and is tightly fitted in the reservoir 11. Side wall of the heat-insulation layer 63 and inner wall of reservoir 11 are circularly sealed therebetween. The whole preheating device 6 is sealed in the reservoir 11 via the stopper 4.

The heat-conductive layer 62 seals the solid tobacco substance in the reservoir, and contacts solid tobacco substance. The guiding tube 3 is inserted in the reservoir 11 and respectively penetrates through the heat-insulation layer 63, heating layer 61, and heat-conductive layer 62. The heat-conductive layer 62 and the outer wall of the guiding tube 3 are engaged by interference fit with seal material inserted therebetween.

The heating layer 61 is used to generate heat and transmit to the heat-conductive layer 62. The heating layer 61 is disposed between the heat-conductive layer 62 and the heating-insulation layer 63. Material for the heating layer 61 is an electric heat wire, electric heat film, or electric heat coating, and in this embodiment, is an electric heat wire. A positive electrode and negative electrode of the heating layer are respectively connected with the electrode element 14 and the connection element 13. For smoking, a control circuit in the power supply part actuates the heating layer 61 to generate heat. The solid tobacco substance has a melt temperature at a range from 42 degree Celsius to 62 degree Celsius, so a heating temperature of the heating layer 61 is offered to melt the solid tobacco substance, such as slightly above 62 degree Celsius.

Since tobacco substance is solidified and stored in the reservoir 11 at first, at an normal temperature, fluid leakage will not take place. In use, the melted tobacco substance is sealed and separated in the reservoir 11 by the preheating device 6, and the stopper 4 at one end of the reservoir 11 is further sealed the preheating device 6 in the reservoir, in such way that tobacco substance is doubly sealed and separated, tobacco substance difficultly leaks out, and a favorable leakage-proof is thus obtained.

The filter layer and the cap 5 or 5" constitute the filter device. The liquefied tobacco substance is guided from reservoir 11 to atomizer 21 which vaporizes the liquid drops into aerosol mixed with tobacco particles. The aerosol flows into the aerosol passage 12, and are first filtered by the filter plate 121. The aerosol passes through the filter hole 122 of the filter plate 121 to next part of the aerosol passage, while aerosol flows to the filter plate 121 and thus confronts resistance thereof, tobacco particles mixed in aerosol deposit on the filter plate 121, so that tobacco particles are filtered from aerosol. Then, aerosol remains to flow along the passage 12, and is secondly filtered by the cap 5. Aerosol flows from the passage 12, then passes from the air slot 53 and through the suction hole 54, and finally flows to outside of shell 1. Or, aerosol flows from the passage 12 and through the air slot 53", then directly to outside of shell 1. Since air slot 53 or 53" exists, which provides resistance to the movement of the aerosol, other tobacco particles are deposited in the air slot 53 or 53' for the purpose of being filtered and so as to prevent more tobacco particles flowing to outside of the shell 1 or being inhaled to human body.

In the view of disclosure to the embodiments of the present invention, it will be apparent to one skilled in the art that modifications and/or substitutes may be made without departing from the scope and spirit of the invention.

What is claimed is:

1. A mouthpiece device of an electronic cigarette comprising:
   an inhaling shell with an inhaling end and an opposite connection end, and a cap covered at the inhaling end of the inhaling shell; and within the inhaling shell further comprising:
   an atomizing device for vaporizing tobacco substance into aerosol and disposed in the connection end of the inhaling shell;
   a reservoir for storing tobacco substance and forming a first opening at the inhaling end of the inhaling shell and a second opening opposite to the first opening and facing the atomizing device;
   an aerosol passage defined beside the reservoir for transmitting aerosol from the atomizing device to an outside of the inhaling shell, the aerosol passage forming a third opening at the inhaling end of the inhaling shell to be coplanar with the first opening, and a fourth opening opposite to the third opening and facing the atomizing device to be coplanar with the second opening;
   a stopper disposed at the second opening of the reservoir;
   a preheating device for preheating the tobacco substance stored in the reservoir, the preheating device disposed at the second opening between the stopper and the tobacco substance in the reservoir;
   a guiding tube with one end penetrating though the stopper and the preheating device and extending in the reservoir and the other end extending toward the atomizing device so as to guide and transmit the tobacco substance into the atomizing device for vaporization;
   wherein the cap defines a suction hole therethrough for passing aerosol from the third opening of the aerosol passage to outside of the inhaling end for user's suction, the cap is inserted at the inhaling end of the inhaling shell and removably seals the first opening of the reservoir; the cap defines an air slot for depositing tobacco particles on a surface of the air slot; the suction hole is communicated with the aerosol passage via the air slot, and the air slot is stepwise and shaped as letter Z.

2. The mouthpiece device according to claim 1, wherein solid tobacco substance is stored in the reservoir, the solid tobacco substance is capable of being melted into liquid tobacco substance, and the liquid tobacco substance is capable of being transmitted to the atomizing device by the guiding tube for vaporization; the preheating device comprises a heat-insulation layer, a heating layer and a heat-conductive layer; the heating layer is disposed between the heat-insulation layer and the heat-conductive layer; the heat-insulation layer is positioned at the second opening of the reservoir where the guiding tube is inserted, and is tightly engaged with the reservoir for sealing; and the heat-conductive layer is disposed next to and seals the solid tobacco substance and the generated liquid tobacco substance in the reservoir.

3. The mouthpiece device according to claim 2, wherein material of the heating layer is electric heat wire, electric heat film or electric heat coating; a positive electrode and a negative electrode of the heating layer are respectively and electrically connected with a power supply part of the electronic cigarette whereby the heating layer is actuated to generate heat for melting the solid tobacco substance.

4. The mouthpiece device according to claim 2, wherein the guiding tube respectively penetrates the heat-insulation layer, the heating layer and the heat-conductive layer; and the heat-conductive layer is engaged with the guiding tube by an interference fit; and sealing material is circularly inserted between the heat-conductive layer and the guiding tube.

5. The mouthpiece device according to claim 1, wherein the stopper defines a tube hole, the guiding tube is engaged in the tube hole by the interference fit with sealing material circularly inserted therebetween.

6. The mouthpiece device according to claim 1, wherein the atomizing device comprises an atomizing cup with an atomizing chamber therein, and an atomizer held in the atomizing chamber for vaporizing the liquid tobacco substance transmitted via the guiding tube into aerosol; the atomizing cup is intergrated and inseparable, and is made from silica gel whereby the atomizing cup has good heat resistance and heat insulation.

7. The mouthpiece device according to claim 6, wherein the atomizing cup is shaped as a cylinder, adapted for an inner wall of the inhaling shell; the atomizing cup comprises a mounting seat disposed in the atomizing chamber for holding the atomizer, and defines wire-through holes for passing electric wire; the wire-through holes are communicated with said atomizing chamber; and the atomizing cup further centrally defines a through heat-dissipation hole, the mounting seat integrally extends from a bottom of the atomizing chamber away from the atomizing cup for a preset distance to engage with the atomizer.

8. The mouthpiece device according to claim 1, further comprising a filter device set in the inhaling shell for depositing tobacco particles in aerosol.

9. The mouthpiece device according to claim 8, wherein the filter device comprises a filter layer, and the filter layer is set on an inner wall of the aerosol passage according to a cross section of the aerosol passage.

10. The mouthpiece device according to claim 6, wherein the atomizer comprises an electric heat rod and an electric heat wire winding around the heat rod; and the electric heat wire is mounted in the atomizing cup by means of the heat rod.

11. The mouthpiece device according to claim 2, wherein the solid tobacco substance has a melt temperature at a range from 42 degree Celsius to 62 degree Celsius, a heating temperature of the heating layer is offered to melt the solid tobacco substance slightly above 62 degree Celsius.

12. A mouthpiece device of an electronic cigarette comprising:
    an inhaling shell with an inhaling end and an opposite connection end;
    a cap removably covered at the inhaling end of the inhaling shell; and
    within the inhaling shell further comprising:
        an atomizing device for vaporizing tobacco substance into aerosol and disposed in the connection end of the inhaling shell;
        a reservoir for storing tobacco substance;
        an aerosol passage defined beside the reservoir for transmitting aerosol from the atomizing device to an outside of the inhaling shell;
        a stopper disposed at a first end of the reservoir to seal the tobacco substance in the reservoir;
        a preheating device disposed behind the stopper and facing the tobacco substance in the first end of the reservoir;
        a guiding tube with one end penetrating though the stopper and the preheating device and extending in the reservoir and the other end extending toward the atomizing device so as to guide and transmit the tobacco substance into the atomizing device for vaporization;
        wherein the cap seals a second end of the reservoir, defines a suction hole therethrough for passing aerosol from the aerosol passage to outside of the inhaling end for user's suction, the cap defines an air slot for depositing tobacco particles on a surface of the air slot; the suction hole is communicated with the aerosol passage via the air slot, and the air slot is stepwise and shaped as the letter Z.

13. The mouthpiece device according to claim 12, wherein tobacco substance is in solid and/or liquid melted from the solid.

14. A mouthpiece device of an electronic cigarette comprising an inhaling shell with an inhaling end and an opposite connection end for connection with a power supply part of the electronic cigarette, a cap removably covered at the inhaling end of the inhaling shell for user's suction, an atomizing device for vaporizing tobacco substance into aerosol and disposed within the inhaling end of the inhaling shell, a reservoir defined in the inhaling shell for storing tobacco substance, an aerosol passage defined in the inhaling shell and beside the reservoir for transmitting aerosol from the atomizing device to an outside of the inhaling shell, a stopper sealing one end of the reservoir and facing the atomizing device, and a guiding tube with one end penetrating though the stopper and extending in the reservoir and the other end extending toward the atomizing device so as to guide and transmit the tobacco substance into the atomizing device for vaporization; wherein the cap removably seals another end of the reservoir opposite to the stopper, defines a suction hole therethrough for passing aerosol from the aerosol passage to outside of the inhaling end for user's suction, and further defines a stepwise air slot shaped as a letter Z for depositing tobacco particles on a surface of the air slot; the suction hole is communicated with the aerosol passage via the air slot.

* * * * *